United States Patent
Blair

(10) Patent No.: US 11,872,197 B2
(45) Date of Patent: Jan. 16, 2024

(54) METHOD OF TREATMENT OR ALLEVIATING SYMPTOMS OF A DISORDER WITH CURCUMIN

(71) Applicant: Another Chance Nutra, LLC, Wellington, CO (US)

(72) Inventor: Emek Blair, Wellington, CO (US)

(73) Assignee: Another Chance Nutra, LLC, Wellington, CO (US)

( * ) Notice: Subject to any disclaimer, the term of this patent is extended or adjusted under 35 U.S.C. 154(b) by 170 days.

(21) Appl. No.: 17/186,963

(22) Filed: Feb. 26, 2021

(65) Prior Publication Data

US 2021/0275468 A1    Sep. 9, 2021

Related U.S. Application Data

(60) Provisional application No. 62/984,692, filed on Mar. 3, 2020.

(51) Int. Cl.
| | |
|---|---|
| *A61K 31/12* | (2006.01) |
| *A61K 9/00* | (2006.01) |
| *A61P 35/00* | (2006.01) |
| *A61K 9/127* | (2006.01) |
| *A61P 3/00* | (2006.01) |
| *A61K 31/192* | (2006.01) |
| *A61K 31/353* | (2006.01) |
| *A61K 31/343* | (2006.01) |
| *A61K 31/352* | (2006.01) |
| *A61K 31/00* | (2006.01) |

(52) U.S. Cl.
CPC ............ *A61K 31/12* (2013.01); *A61K 9/0053* (2013.01); *A61K 9/127* (2013.01); *A61K 31/192* (2013.01); *A61K 31/343* (2013.01); *A61K 31/352* (2013.01); *A61K 31/353* (2013.01); *A61K 31/658* (2023.05); *A61P 3/00* (2018.01); *A61P 35/00* (2018.01)

(58) Field of Classification Search
None
See application file for complete search history.

(56) References Cited

U.S. PATENT DOCUMENTS

| | | |
|---|---|---|
| 2011/0257126 A1 | 10/2011 | Neven et al. |
| 2018/0169069 A1 | 6/2018 | Bascomb et al. |
| 2018/0318217 A1* | 11/2018 | Kurzrock ............... A61P 29/00 |
| 2020/0009067 A1 | 1/2020 | Hoffman et al. |
| 2020/0316015 A1* | 10/2020 | Green ................. C12Q 1/6895 |
| 2021/0220301 A1* | 7/2021 | Sathyavageeswaran .................... A61K 31/12 |
| 2021/0236575 A1* | 8/2021 | Garabagi ............... A61K 9/006 |

FOREIGN PATENT DOCUMENTS

WO    WO 2017/127333 A1    7/2017

OTHER PUBLICATIONS

PCT International Patent Application No. PCT/US21/20696, International Search Report and Written Opinion of the International Searching Authority dated Jun. 7, 2021, 7 pages.

* cited by examiner

*Primary Examiner* — Celeste A Roney
(74) *Attorney, Agent, or Firm* — Craig R. Miles; CR MILES P.C.

(57) ABSTRACT

A method of treating or alleviating symptoms of disease, disorder or condition associated body wasting in a subject, including disease, disorder or condition associated body wasting in the subject, the disorder or condition identified based on initial measures of body mass, body mass index, or a bloodstream concentration of a substance, orally administering to said subject an amount of curcumin over a period of time effective treat or alleviate the disease, disorder or condition associated body wasting, diminishing or reversing the body wasting in the subject, and assessing efficacy of treating or alleviating symptoms of the disease, disorder or condition associated with body wasting by comparing final measures of body mass, body mass index, or a bloodstream concentration of a substance after the treatment period time to the initial measures of body mass, body mass index, or bloodstream concentration of the substance.

13 Claims, 4 Drawing Sheets

METHOD OF TREATMENT OR ALLEVIATING SYMPTOMS OF A DISORDER WITH CURCUMIN

This United States Non-Provisional Patent Application claims the benefit of U.S. Provisional Patent Application No. 62/984,692, filed Mar. 3, 2020, hereby incorporated by reference herein.

I. FIELD OF THE INVENTION

A method of treating or alleviating symptoms of a disease, disorder or a condition in a subject including orally administering to the subject an amount curcumin effective to diminish or reverse body mass loss in an animal.

II. BACKGROUND OF THE INVENTION

Identification, treatment and alleviating symptoms of body wasting alone or associated with diseases, disorders or conditions has historically been limited by the lack of a widely accepted definitions of various weight loss or disease associated weight loss disorders or conditions. Unintended weight loss can occur from malnutrition due to anyone or a combination of disorders or conditions such as: malabsorption of nutrients, anorexia nervosa, or anorexia, sarcopenia, or age-related muscle loss, or multifactorial syndromes such as cachexia defined by an ongoing loss of skeletal muscle mass that may be partially but not necessarily reversed by conventional nutritional support, or combinations thereof. Accordingly, accurate epidemiological data on the prevalence of body wasting may be lacking due to changing diagnostic criteria and under-identification of people with a particular body wasting disease, disorder or condition. However, body wasting from any disease, disorder or condition is estimated to affect more than five million people in the United States.

The prevalence of body wasting due solely to cachexia is growing and estimated at about one percent (1%) of the United States population. The prevalence may be lower in Asia but due to the larger population, represents a similar burden. Cachexia is also a significant problem in South America and Africa. The most frequent causes of cachexia in the United States by population prevalence are: 1) chronic obstructive pulmonary disease ("COPD"), 2) heart failure, 3) chronic kidney disease, and 4) cancer, and combinations thereof. The prevalence of cachexia ranges from about 15% to about 60% among people with cancer, increasing to an estimated 80% in terminal cancer.

Cachexia can contribute to significant loss of function and healthcare utilization. Estimates using the National Inpatient Sample in the United States suggest that cachexia accounted for approximately 170,000 hospital stays in 2016. Cachexia is considered the immediate cause of death of many people with cancer, estimated between about 20% to about 40%.

Although there are numerous mouse and animal studies on curcumin, there are limited human studies and no credible randomized controlled human studies assessing efficacy of curcumin to treat or alleviate symptoms of a disease, disorder or a condition in a subject by orally administering curcumin an amount effective in the subject to prevent, reduce progression, or reverse body wasting, and in particular body wasting due to cachexia.

There is a long felt but unresolved need to treat or alleviate symptoms of body wasting whether due to malabsorption of nutrients, anorexia nervosa, or anorexia, sarcopenia, or age-related muscle loss, or multifactorial syndromes such as cachexia by oral administration of a nutraceutical.

There would be a substantial advantage in a method of treating or alleviating symptoms of body wasting by oral administration of curcumin, because curcumin offers, without a prescription, a non-toxic remedy having no known fatal overdose levels and which is virtually side effect free, outside of the therapeutic benefit.

III. SUMMARY OF THE INVENTION

Accordingly, a broad object of particular embodiments of the invention can be to afford a method of treating or alleviating symptoms of a disease, disorder or a condition associated with body wasting in a subject, comprising, consisting essentially of, or consisting of orally administering to a subject a dosage of curcumin in an amount effective in the subject to diminish or reverse body wasting or increase survival rate, and combinations thereof.

Naturally, further objects of the invention are disclosed throughout other areas of the specification, drawings, photographs, and claims.

IV. BRIEF DESCRIPTION OF THE DRAWINGS

V. DETAILED DESCRIPTION OF THE INVENTION

Figure 1:
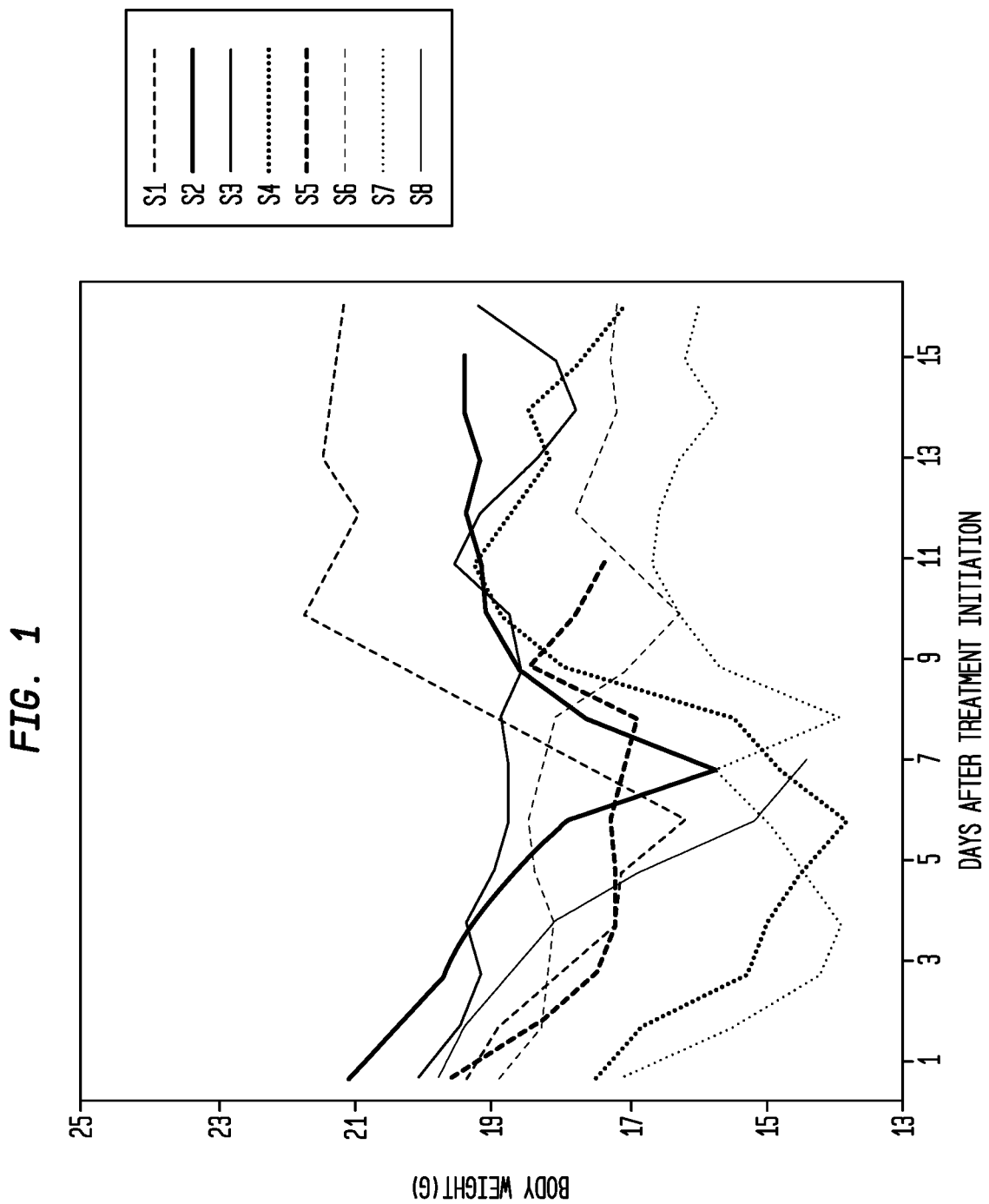
FIG. 1 is a graph which plots body mass of subjects in an experimental group against days after initiation of daily oral administration of curcumin 50 mg/kg body mass.
Figure 2:
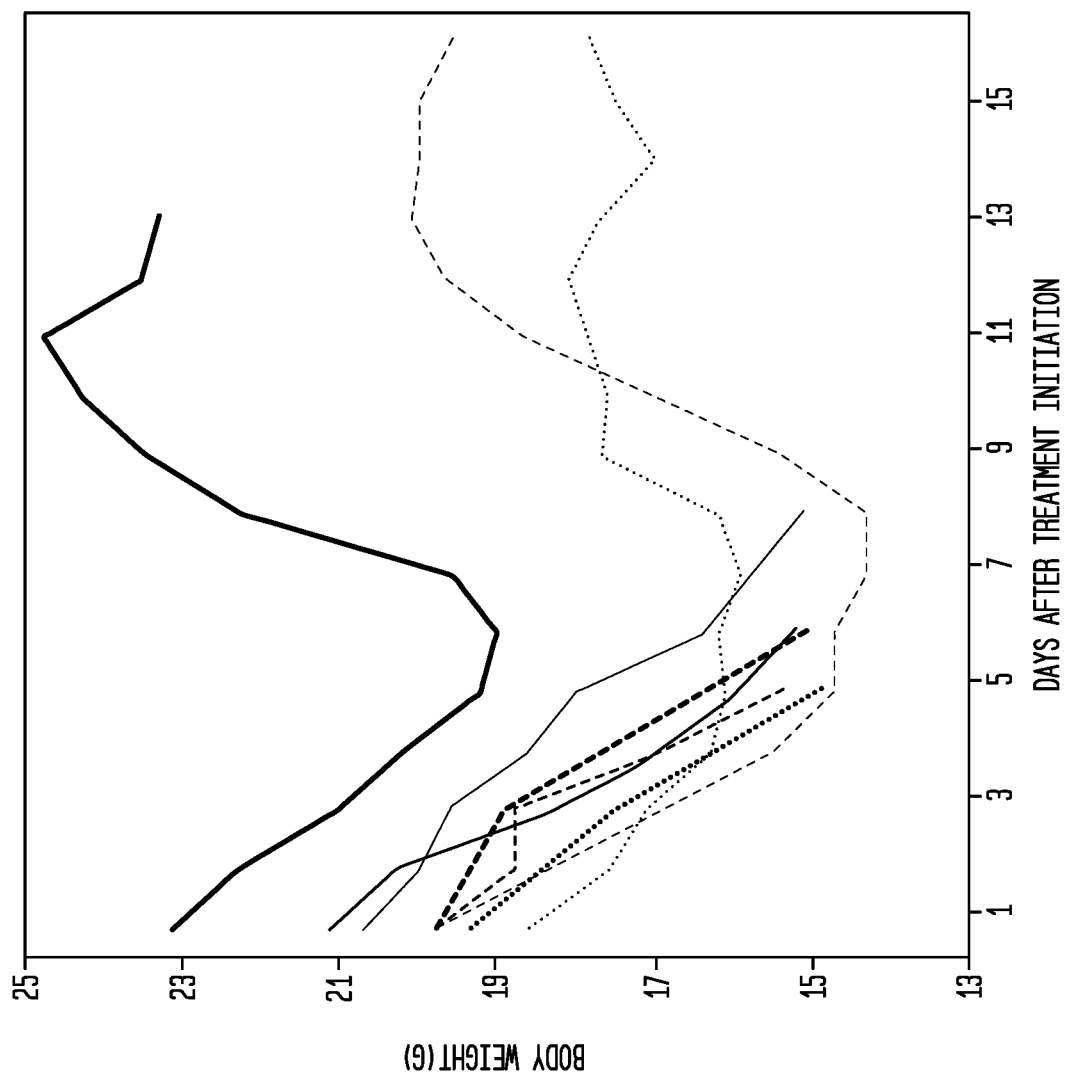
FIG. 2 is a graph which plots body mass of subjects in a control group against days after initiation of oral administration of a phosphate buffered saline placebo 50 mg/kg body mass.
Figure 3:
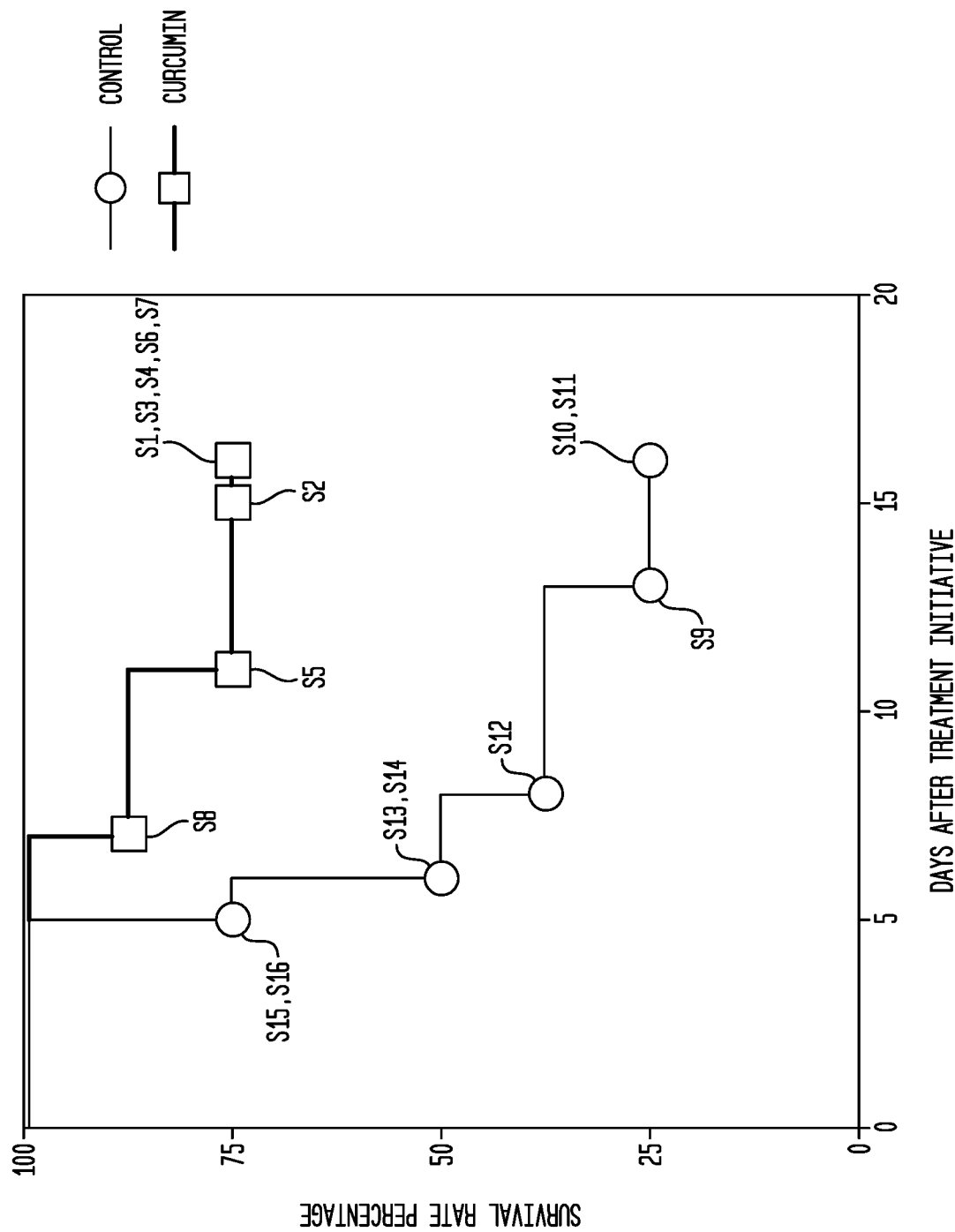
FIG. 3 is a graph which plots subject survival rate percent against days after identifying a disease related body mass loss of five percent defining disease associated body wasting.

With general reference to FIGS. 1 through 4, the inventive method includes embodiments of treating or alleviating symptoms of a disease, disorder or condition associated body wasting or unintended body mass loss in a subject comprising, consisting essentially of, or consisting of administering to the subject an amount of curcumin effective in the subject to diminish or prevent disease, disorder, or condition associated body wasting or unintended body mass loss. Specifically, a method of treating or alleviating symptoms of cancer associated cachexia in a subject comprising, consisting essentially of, or consisting of orally administering to the subject an amount curcumin effective in the subject to diminish or prevent cancer associated cachexia.

"A" or "an" entity means one or more of that entity; for example, "a polymer" refers to one or more polymers or at least one polymer. As such, the terms "a" or "an", "one or more" and "at least one" can be used interchangeably herein. Furthermore, the language "selected from the group consisting of" refers to one or more of the elements in the list that follows, including combinations of two or more of the elements.

"About" means that ranges may be expressed as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. In the context of such a numerical value or range "about" means plus or minus 10% of the numerical value or range recited or claimed unless otherwise specified, or the values within the range are incrementally divided into lesser percentage between ranges or values.

"Administration" or "Administering" for the purposes of this invention means delivery of a curcumin dosage to a subject, and without sacrificing the breadth of the foregoing, includes as examples: orally, respiratorily, intratracheally, nasopharyngeally, intravenously, intraperitoneally, subcutaneously, intracranially, intradermally, intramuscularly, intraocularly, intrathecally, intracerebrally, intranasally, infusion, orally, rectally, intravenously, intracutaneously, transdermally, implant, and combinations thereof.

"Blood Substance" for the purposes of this invention means a substance in blood, and without sacrificing the breadth of the foregoing can include circulating levels of pro-inflammatory cytokines, particularly Interleukin-6.

"Bloodstream Concentration" for purposes of this invention means an amount of a particular blood substance in a specific amount of blood, and without sacrificing the breadth of the foregoing, can be expressed as kilograms/meter3 (milligrams per deciliter (mg/dL)) or equivalent measure.

"Body mass" for the purposes of this invention means a subject's weight.

"Body mass index" is calculated by the following formula: mass (kg)/(height (m)$^2$).

"Body Wasting" for the purposes of this invention means body mass loss in a subject not actively trying to lose body mass characterized by loss of muscle or fat, and without sacrificing the breadth of the foregoing includes as illustrative examples cachexia, sarcopenia, denervation-induced wasting, muscle wasting, or other forms of wasting, or combinations thereof.

"Cachexia" for the purposes of this invention means a disease, disorder or condition associated body mass loss of muscle with or without loss of fat mass. Cachexia while generally associated with increased protein catabolism due to underlying disease(s), disorder(s) or condition(s), it may also be associated with contributory factors to the onset of cachexia such as anorexia and metabolic alterations with examples including increased inflammatory status, increased muscle proteolysis and impaired carbohydrate, protein and lipid metabolism. A prominent clinical feature of cachexia can be body mass loss in adults (optionally, corrected for fluid retention) or growth failure in children (excluding endocrine disorders). Cachexia can be associated with or result from (directly or indirectly) various underlying diseases, disorders, or conditions including cancer, metabolic acidosis (from decreased protein synthesis and increased protein catabolism), certain infectious diseases (such as, bacterial infections, including tuberculosis, AIDS), autoimmune disorders, addiction to drugs such as amphetamines or cocaine, chronic alcoholism and/or cirrhosis of the liver, chronic inflammatory disorders, anorexia, neurological conditions and/or neurodegenerative disease. Cachexia can be identified or diagnosed based on one or more of the following:

Weight loss of at least 5% over a period of six months (in the absence of starvation);
A BMI <20 together with weight loss; or
Appendicular skeletal muscle index consistent with sarcopenia (males <7.26 kg/m2; females <5.45 kg/m2) together with weight loss; however, this is not intended to preclude identifying or diagnosing cachexia based on other measures or factors, or combinations thereof.

"Cannabinoid" for the purposes of this invention means cannabinol, cannabinolic acid, Δ(9)-tetrahydrocannabinol, Δ(9)-tetrahydrocannabinolic acid, Δ(9)-cannabidiol, Δ(9)-tetrahydrocannabidiolic acid, Δ(8)-tetrahydrocannabinol, Δ(8)-tetrahydrocannabinolic acid, Δ(8)-tetrahydrobannabidiol, Δ(8)-tetrahydrocannacbidiolic acid, Δ(9)-tetrahydrocannabivarin, cannabigerol, cannabidigerolic acid, cannabichromene, cannabichromenic acid, cannabicyclol, cannabicyclolic acid, cannabielsoin, cannabitriol, nabilone, equivalents, or combinations thereof.

"Cannabidiol (CBD)" for the purposes of this invention means a phytocannabinoid having the formula $C_{21}H_{30}O_2$ having molar mass of 314.464 g/mol and a density of 920 kg/m$^3$ and a CAS ID 13956-29-1. CBD can be obtained as an extract which fulfils the definition of a "botanical drug substance" provided in the *Guidance for Industry Botanical Drug Products*, June 2004, US Department of Health and Human Services, Food and Drug Administration Centre for Drug Evaluation and Research of: "A drug substance derived from one or more plants, algae, or macroscopic fungi,", or combinations thereof. In particular embodiments, CBD can, but need not necessarily, be extracted from a botanical biomass, such as, the stalks, stems and flowers of the *Cannabis sativa* plant. The cannabidiol extracted from a botanical biomass can be a component of a full-spectrum CBD extract which includes all of the cannabinoids extracted from the botanical biomass, or can, but need not necessarily be, a CBD extract which includes only a portion of all of the cannabinoids extracted from the botanical biomass. A CBD extract of a botanical biomass can include CBD by weight occurring in a range of about 20% to about 80%. CBD can, but need not necessarily be, a CBD isolate separated from the full spectrum CBD, which CBC isolate can have a purity in the range of up to about 99% by weight. In particular embodiments, the CBD extract or mixture of CBD extracts of a botanical biomass, or the CBD isolate or a mixture of CBD isolates separated from a CBD extract or mixture of extracts, or synthetic CBD, or combinations thereof can have a weight percent occurring in the range of about 90% to about 99%, or can be selected from the group consisting essentially of or consisting of: about 91% to about 93%, about 92% to about 94%, about 93% to about 95%, about 94% to about 96%, about 95% to about 97%, and about 96% to about 98%. In particular embodiments the CBD extract or CBD isolate can, but need not necessarily, contain an amount of tetrahydrocannabinol ("THC") CAS ID 1972-08-3; however, in particular embodiments the CBD extract, isolate or mixture can, but need not necessarily, contain a weight percent THC in a range of essentially zero to about 0.5%, and in particular embodiments, can contain a weight percent THC of less than 0.05%. In particular embodiments, the weight percent THC can be selected from the range of about 0.01% to about 0.1%, or a weight percent THC selected from the group consisting essentially of or consisting of: about 0.02% to about 0.04%, about 0.03% to about 0.05%, about 0.04% to about 0.06%, about 0.05% to about 0.07%, about 0.06% to about 0.08%, about 0.07% to about 0.09%. In particular embodiments, the CBD can, but need not necessarily, be chemically synthesized and used alone or in combination with CBD extracts or CBD isolates obtained from a botanical biomass.

"Curcumin" for the purposes of this invention means one or more of a diarylheptanoid with the IUPAC name (1E, 6E)-1,7-Bis(4-hydroxy-3-methoxyphenyl) hepta-1,6-diene- 3,5-dione having the chemical formula $C_{21}H_{20}O_6$ (CAS Number 458-37-7) and a molar mass of 368.385 grams per mole with a melting point of 183° C.; IUPAC name (1E, 6E)-1-(4-Hydroxy-3-methoxyphenyl)-7-(4-hydroxyphenyl) hepta-1,6-diene-3,5-dione having a chemical formula $C_{20}H_{18}O_5$ (CAS Number 22608-11-3) and a molar mass of 338.35 grams per mole with a melting point of 226° C. to 231° C.; or IUPAC name (1E,6E)-1,7-Bis(4-hydroxyphenyl) hepta-1,6-diene-3,5-dione having a chemical formula $C_{19}H_{16}O_4$ (CAS Number 24939-16-0) and a molar mass of 308.33 grams per mole and a melting point of 226° C. to 231° C., or combinations thereof (a combination of all three may be referred to as "3 peak curcumin") which can be extracted or isolated from *Curcuma longa* plants or the turmeric root thereof, or biosynthesized along with various analogs and derivatives by modifications of the two aromatic rings containing o-methoxy phenolic groups or the seven-carbon linker of an α,β-unsaturated β-diketone.

"Combination or combining" for the purposes of this invention means any method of putting two or more materials together. Such methods include, but are not limited to, mixing, blending, commingling, concocting, dispersing, homogenizing, incorporating, intermingling, fusing, joining, shuffling, stirring, coalescing, integrating, confounding, joining, uniting, or the like.

"Complex" for the purposes of this invention means a molecular entity formed by chemical association involving two or more component molecular entities.

"Condition" for the purposes of this invention means the measurable state of a subject within normative values for a particular measured state.

"Disease" or "Disorder" for the purposes of this invention means a disease or ailment of a subject characterized by measurable values outside of the normative values for the subject, and without sacrificing the breadth of the foregoing, includes one or more of cachexia, sarcopenia, muscle wasting or other forms of insufficient body mass which may, but need not necessarily, be associated with one or more of: age, cancer, metabolic acidosis, infectious disease, diabetes, human immunodeficiency virus (HIV), autoimmune deficiency syndrome (AIDS), autoimmune disorders, liver disease (such as, cirrhosis of the liver), chronic inflammatory disorders, anorexia, heart disease, kidney disease, lung disease, osteoporosis, skeletal muscle disease, motor neuron disease, multiple sclerosis, muscle atrophy, malnutrition, low birth weight, inactivity or disuse, drug toxicity, burns, parasitic infection, trauma, surgery, nerve and vessel damage and neurodegenerative diseases such as myasthenia gravis, Guillain-Barre syndrome, Lou Gehrig's disease, muscular dystrophy and spinal cord injuries.

"Dosage" for the purposes of this invention means an amount of curcumin recommended to be taken at a particular time, and without sacrificing the breadth of the foregoing, the dosage may be administered as a dosage unit form comprising one or more of powders, liquids, gels, tablets, troches, pills, capsules which may also contain additional agents as examples one or more of: a cannabinoid, a cannabidiol, a terpene; a binder such as gum, acacia, corn starch or gelatin; excipients such as dicalcium phosphate; a disintegrating antagonist such as corn starch, potato starch, alginic acid and the like; a lubricant such as magnesium stearate; a sweetening antagonist such as sucrose, lactose or saccharin may be added; a taste mask; and preservatives, and when the dosage unit form comprises a capsule, it may contain a liquid or organic carrier, and when the dosage unit form comprises a capsule, tablet or pill various other materials may be present such as coatings or to otherwise modify the physical form of the dosage unit, for example, tablets, pills, or capsules may be coated with shellac, sugar or both. The dosage may be admixed with a syrup, an elixir, or food composition.

"Effective" for the purposes of this invention means effecting change in a measurable value.

"Effective amount" for the purposes of this invention means an amount effective at dosages in one or more administrations and for periods of time necessary effect change in a measurable value in the subject.

"Equivalent" for the purposes of this invention means a drug or chemical containing similar amounts of the same ingredients as another drug or chemical or having similar chemical structures, properties or functions to another drug or chemical.

"Hemp" for the purposes of this invention means *Cannabis sativa*, also referred to as industrial hemp, plant of the family Cannabaceae.

"Lipid" for the purposes of this invention means a substance insoluble in water and soluble in alcohol, ether, and chloroform and without limitation to the breadth of the foregoing include fatty acids, neutral fats, waxes and steroids (like cortisone), compound lipids (lipids complexed with another type of chemical compound) including, but not necessarily limited to, lipoproteins, glycolipids and phospholipids which may, but need not necessarily, be derived from botanical biomass such as sunflower seed, rapeseed, egg, soy, algae, or animal biomass such as fish, or combinations thereof.

"Liposome" for the purposes of this invention means an aggregate of molecules comprising at least one lipid bilayer having the nonpolar region of the molecules of the bilayer sequestered between the polar or charged groups of the molecules which afford an inner shell surrounding an aqueous solution core and outer shell in contact with an aqueous solution. Hydrophilic substances dissolved in the core do not readily pass through the bilayer. Hydrophobic substances associate with the bilayer. A liposome or plurality of liposomes, whether separate or in aggregate, can be loaded with hydrophobic or hydrophilic molecules, or a combination thereof, or form a complex with hydrophobic or hydrophilic molecules, or be combined with hydrophobic or hydrophilic molecules. To deliver the molecules to a site of action, the lipid bilayer can fuse with other bilayers such as cell membranes, allowing delivery of the liposome contents, or complexed or combined molecules.

"Liposomal curcumin" for the purposes of this invention means a liposome containing, complexed with or combined with an amount of curcumin, and without sacrificing the breadth of the forgoing can be curcumin contained in the aqueous core or lipid bilayer of a liposome, curcumin as a complexed with a liposome, or curcumin combined with liposome even if not contained in or complexed with a liposome, or combinations thereof in a composition.

"Micelle" for the purposes of this invention means an aggregate of molecules having both polar or charged groups or molecules and nonpolar regions or molecules, where the polar or ionic groups or molecules form an outer shell in contact with a solution, and the nonpolar region or molecules are sequestered on the interior of the shell. A micelle can contain, be complexed with, or combined with hydrophobic or hydrophilic molecules. To deliver the molecules to a site of action, the micelle can fuse with other bilayers such as cell membranes, allowing delivery of the micelle contents, or complexed or combined molecules.

"Micellular curcumin" for the purposes of this invention means a micelle containing, complexed with or combined with an amount of curcumin, and without sacrificing the breadth of the forgoing can be curcumin contained in a micelle, curcumin as a complexed with a micelle, or curcumin combined with liposome even if not contained in or complexed with a liposome, or combinations thereof in a composition.

"Oral" or "Orally" for the purposes of this invention means delivered through the cavity of the mouth.

"Subject" for the purposes of this invention includes humans and non-human animals and without sacrificing the breadth of the foregoing includes as illustrative examples: an equine, a bovine, a sheep, a porcine, a donkey, a deer, a canine, a feline, a mouse, a rat, a guinea pig, whales, dolphins, and a fish.

"Symptom" for the purposes of this invention means a physical or mental feature regarded as indicating a condition of a disease or a condition of a subject.

"Taste Mask" for the purposes of this invention means an agent(s) useful to mask the taste of an orally administered drug, medicament, substance, or curcumin, liposomal curcumin, micellular curcumin, and without limitation to the foregoing, such as anethole, dihydroanethole, eugenol, wintergreen, vanillin, ethylvanillin, ethyl maltol, or the like.

"Terpene" for the purposes of this invention means alpha-pinene, beta-pinene, myrcene, limonene, carophyllene, linalool, alpha bisabolol, delta 3 carene, borneol, eucalyptol, terpineol, camphene, nerolidol, terpinolene, valencene, humulene, geraniol, phellandrene, fenchol, phytol, sabinene, camphor, menthol, isoborneol, cedrane, guaiol, isopulegol, geranyl acetate, cymene, pulegon, citral, equivalents, or combinations thereof.

"Treating" or "Treatment" for the purposes of this invention means management and care of a subject with respect to occurrence or recurrence of body wasting or unintended body mass loss which may be associated with a disease, disorder or condition in a subject, reducing the severity, extent or duration of body wasting or unintended body mass loss which may be associated with a disease, disorder or condition in a subject.

"Unintended body mass loss" for the purposes of this invention means body mass loss in a subject without actually attempting to reduce body weight, and without sacrificing the breadth of the foregoing, one suitable measure of unintended body mass loss in a subject can be body mass index of less than 18.5; or body mass loss of about five percent (5%) or greater.

Figure 4:
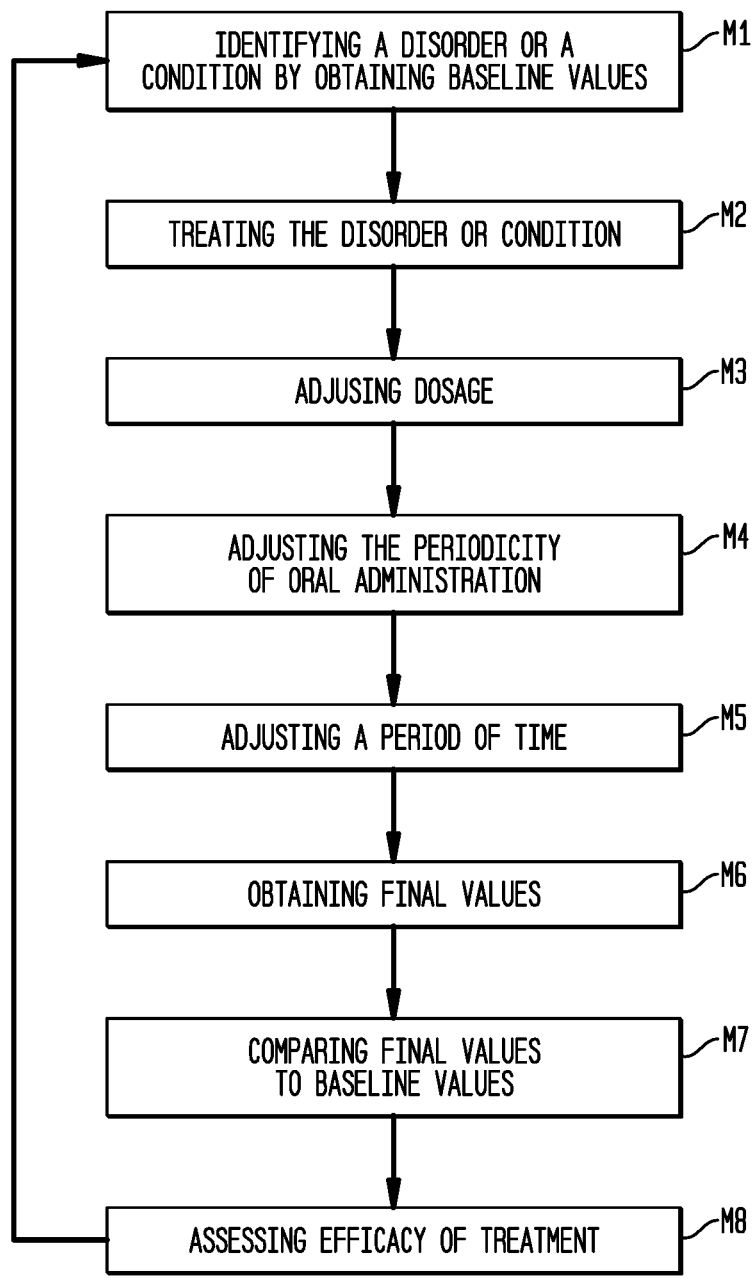
FIG. 4 is a block flow diagram of an embodiment of a method of treatment or alleviating symptoms of disease related body wasting.

Now, with primary reference to FIG. 4, the method can include obtaining measures of initial baseline values identifying a disease, disorder or condition-associated body wasting or of body wasting, or symptoms thereof, in or of a subject such as body mass loss, body mass index, or a blood substance, or combinations thereof (Block M1).

The method can further include treating the disease, disorder or condition-associated body wasting, body wasting, cachexia, or alleviating symptoms of the disease, disorder or condition-associated body wasting, body wasting, or cachexia, by administering to the subject an amount of curcumin over a period of time (Block M2). In particular embodiments a curcumin dosage can comprise, consist essentially of, or consist of an amount of curcumin, liposomal curcumin, or micellular curcumin, or mixtures thereof in a range of about 10 milligrams per kilogram ("mg/kg") of body mass of the subject to about 100 mg/kg of body mass in the subject. In particular embodiments, the amount of curcumin dosage can be selected from the group consisting of: about 11 milligrams to about 20 milligrams, about 15 milligrams to about 25 milligrams, about 20 milligrams to about 30 milligrams, about 25 milligrams to about 35 milligrams, about 30 milligrams to about 40 milligrams, about 35 milligrams to about 45 milligrams, about 40 milligrams to about 50 milligrams, about 45 milligrams to about 55 milligrams, about 50 milligrams to about 60 milligrams, about 55 milligrams to about 65 milligrams, about 60 milligrams to about 70 milligrams, about 65 milligrams to about 75 milligrams, about 70 milligrams to about 80 milligrams, about 75 milligrams to about 85 milligrams, about 80 milligrams to about 90 milligrams, about 85 milligrams to about 95 milligrams, or combinations thereof.

In particular embodiments, the method can further include adjusting the curcumin dosage based on one or more of: the form of curcumin administered, the dosage unit form, and the route of administration (Block M3). As an illustrative example, oral administration of liposomal curcumin can provide the substantial advantage of a reduced curcumin dosage. In particular embodiments, the curcumin dosage can comprise, consist essentially of, or consist of oral administration of liposomal curcumin in the range of about 40 mg/kg of body mass to about 60 mg/kg of body mass of a subject, and in particular embodiments liposomal curcumin of about 50 mg/kg of body mass of a subject.

In particular embodiments, the method can further include adjusting the periodicity of administration (Block M4). The periodicity of oral administration can be adjusted based on curcumin form, administered dosage unit form, and curcumin dosage. In particular embodiments, the periodicity of oral administration can occur within the range of three times daily to once every seven days. In particular embodiments, the periodicity of oral administration can be selected from the group including, consisting essentially of, or consisting of: twice daily, once daily, once every two days, once every three days, once every four days, once every five days, once every six days. As one illustrative example, the method can include once daily oral administration of liposomal curcumin in the range of 40 mg/kg body mass to 60 mg/kg body mass to achieve efficacious results over a period of time.

In particular embodiments, the method can include adjusting a period of time over which periodic administration of the curcumin dosage occurs (Block M5). The period of time can be coordinated with the form of curcumin, the curcumin dosage, and dosage unit form. In particular embodiments, oral administration of a curcumin dosage at a particular periodicity of administration can be maintained indefinitely in the absence of any adverse events or side effects. In particular embodiments, the curcumin dosage may be administered as a prophylactic treatment to stop disease or ill health from occurring, and as an illustrative example, the curcumin dosage may be administered before symptoms of a disease or condition occur and administration may occur daily, semi-daily, or weekly for a period of a few months to a few years (1 year, 2 years, 3 years, 4 years, 5 years . . . ). In particular embodiments, the method can include a period of time within the range of consecutive 10 days to 60 days. Depending on the curcumin dosage form, the curcumin dosage the periodicity of oral administration can be selected from the group including, consisting essentially of or consisting of: about 11 days to about 20 days, about 15 days to about 25 days, about 20 days to about 30 days, about 25 days to about 35 days, about 30 days to about 40 days, about 35 days to about 45 days, about 40 days to about 50 days, about 45 days to about 55 days, and about 50 days to about 59 days. As one illustrative example, in determining efficacy of once daily oral administration of liposomal curcumin at a curcumin dosage of about 50 mg/kg body mass an efficacious period of time can be about 10 to about 20 days.

The method can further include obtaining final values of measures of the disease, disorder or condition-associated body wasting, body wasting, such as cachexia, or symptoms thereof, after a period of treatment in accordance with embodiments of the method including for example one or more of body mass, body mass index, or blood substance (Block M6).

The method can further include comparing the final values with the corresponding initial baseline values. As one illustrative example shown by FIG. 2, final values of measured body mass of subjects after a period of treatment in accordance with and embodiment of the method can be compared to corresponding baseline values of measured body mass of subjects prior to treatment with an embodiment of the method (Block M7); however, this illustrative example is not intended to preclude embodiments which include a comparison of a lesser or greater number of final values with corresponding initial values associated with subjects treated accordance with an embodiment of the method.

The method can further include assessing efficacy of treating the subject with an embodiment of the method based upon evidence of reduced rate of body mass loss or body mass gain (Block M8). Again, with reference to FIG. 2, as one illustrative example, in particular subjects (Subjects S-1, S-2, S-3, S-4, S-5, S-6), the final values of body mass as compared to the initial values of body mass evidence an increase in body mass.

The method can further include adjusting the amount of curcumin administered to the subject over a second or more periods of time based on assessing efficacy of prior treating the subject (Block M8). Adjusting the amount of curcumin can comprise one or more of changing the curcumin dosage form, changing the curcumin dosage, changing the periodicity of administration of the curcumin dosage, changing the route of administration. As one illustrative example, the curcumin dosage form and the periodicity of administration of the curcumin dosage may remain the same as in the prior treatment, and the curcumin dosage can be increased within the range of about 10 mg/kg body mass to about 100 mg/kg body mass.

The method can further include repeating or continuing treatment in accordance with the method to obtain repeated initial and final values to allow corresponding repeated comparison of initial and final values to assess efficacy of the treatment of a subject using one or more embodiments of the inventive method.

Example I

Experimental Model. The experimental model utilized in the study is the well-characterized model of cancer cachexia: mice bearing the C26 carcinoma. The growth of the C26 tumor causes a marked and progressive loss of body and skeletal muscle mass, accompanied by reduced muscle cross-sectional area and muscle strength. Adipose tissue is also lost. Body wasting can be coincident with elevated circulating levels of pro-inflammatory cytokines, particularly Interleukin-6, which is directly, although not entirely, responsible for C26 cachexia. It is well-accepted that a primary mechanism by which the C26 tumor induces muscle tissue depletion is the activation of skeletal muscle proteolytic systems. Thus, measurement of body mass loss in C26 carcinoma mice represents a reproducible method for the evaluation of the ongoing muscle catabolism.

Materials. Liposomal curcumin was obtained from Valimenta Labs, Wellington, Colo. using a lipid delivery system (CELLg8™ licensed from Nutritional Biomimetics, LLC, Fort Collins, Colo.) of an extract of turmeric root including three peak curcuminoids having a purity of about 95%.

Subjects. Subjects included and experimental group of eight mice (Subjects 1 through 8) and a control group of eight mice (Subjects 9 through 16) all bearing the C26 carcinoma with identified cachexia onset defined by body mass loss of five percent. Exclusion criteria for subjects included body mass loss of less than five percent.

Disease, Disorder or Condition Associated Body Wasting. All of the subjects were mice bearing the C26 carcinoma having identified body wasting evidenced by a body mass loss of five percent prior to measure of the initial value of body mass.

Treatment. Subjects in the experimental group (Subjects 1 through 8) were each orally administered 50 mg/kg of liposomal curcumin once daily for a consecutive fifteen-day period under controlled environmental conditions. Subjects in the control Group (Subjects 9 through 16) were each orally administered 50 mg/kg phosphate buffered saline for a consecutive fifteen-day period under controlled environmental conditions. Body mass of each subject in the experimental group and in the control group was measured once daily.

Results.

Body Mass Gain. Now referring to FIGS. 1 and 2, of the eight subjects in the experimental group under treatment with liposomal curcumin in accordance with an embodiment of the inventive method, six subjects (Subjects S1, S2, S3, S4, S6, and S7) had final values of measured body mass at 15 days that evidenced a body mass gain as compared to the control group in which only three subjects (S9, S10, and S11) had final values of measured body mass that evidenced a body mass gain.

Survival Rate. Now, referring to FIGS. 1 through 3, of the eight subjects in the experimental group, six subjects (Subjects S1, S2, S3, S4, S6, and S7) under treatment with liposomal curcumin in accordance with an embodiment of the inventive method, survived 15 days subsequent to identified cachexia onset, as compared to, only two of the eight subjects (Subjects S10 and S11) in the control group. The difference is significant (p=0.036).

As can be easily understood from the foregoing, the basic concepts of the present invention may be embodied in a variety of ways. The invention involves numerous and varied embodiments of a methods for treating a disorder or alleviating symptom of a disorder by orally administrating an amount of CBD over a period of time including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) methods disclosed and described, ii) similar, equivalent, and even implicit variations of each of these methods, iii) those alternative embodiments which accomplish each of the functions shown, disclosed, or described, iv) those alternative designs and methods which accomplish each of the functions shown as are implicit to accomplish that which is disclosed and described, v) each feature, component, and step shown as separate and independent inventions, vi) the applications enhanced by the various systems or components disclosed, vii) the resulting products produced by such systems or components, viii) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

What is claimed is:

1. A method of treating or alleviating symptoms of body wasting of a subject, comprising:
   identifying said body wasting in said subject; and
   orally administering to said subject an amount of curcumin effective to diminish or reverse said body wasting in said subject.

2. The method of claim 1, wherein said body wasting comprises a disease or disorder associated with body wasting.

3. The method of claim 2, wherein said disease or disorder associated body wasting comprises cachexia.

4. The method of claim 1, further comprising identifying said body wasting by measuring a body mass loss, a body mass index or blood substance.

5. The method of claim 1, wherein said amount of curcumin comprises an amount of isolated curcumin, an amount of liposomal curcumin, micellular curcumin, a curcumin analog, a curcumin derivative, and combinations thereof.

6. The method of claim 1, wherein said amount of curcumin occurs within a range of about 10 milligrams per kilogram of body mass of said subject to about 100 mg/kg of body mass in said subject.

7. The method of claim 6, wherein said amount of curcumin is selected from the group consisting of: about 11 milligrams to about 20 milligrams, about 15 milligrams to about 25 milligrams, about 20 milligrams to about 30 milligrams, about 25 milligrams to about 35 milligrams, about 30 milligrams to about 40 milligrams, about 35 milligrams to about 45 milligrams, about 40 milligrams to about 50 milligrams, about 45 milligrams to about 55 milligrams, about 50 milligrams to about 60 milligrams, about 55 milligrams to about 65 milligrams, about 60 milligrams to about 70 milligrams, about 65 milligrams to about 75 milligrams, about 70 milligrams to about 80 milligrams, about 75 milligrams to about 85 milligrams, about 80 milligrams to about 90 milligrams, about 85 milligrams to about 95 milligrams, or combinations thereof.

8. The method of claim 1, wherein said amount of curcumin admixed with an amount of cannabinoid.

9. The method of claim 8, where said amount of cannabinoid is selected from the group consisting of cannabinol, cannabinolic acid, Δ(9)-tetrahydrocannabinol, Δ(9)-tetrahydrocannabinolic acid, Δ(9)-cannabidiol, Δ(9)-tetrahydrocannabidiolic acid, Δ(8)-tetrahydrocannabinol, Δ(8)-tetrahydrocannabinolic acid, Δ(8)-tetrahydrobannabidiol, Δ(8)-tetrahydrocannacbidiolic acid, Δ(9)-tetrahydrocannabivarin, cannabigerol, cannabidigerolic acid, cannabichromene, cannabichromenic acid, cannabicyclol, cannabicyclolic acid, cannabielsoin, cannabitriol, nabilone, equivalents, or combinations thereof.

10. The method of claim 1, further comprising lipids admixed with said amount of curcumin.

11. The method of claim 1, further comprising a taste mask.

12. The method of claim 1, further comprising increasing body mass of said subject.

13. The method of claim 1, wherein said subject comprises a plurality of subjects, and wherein said method further comprises increasing survival rate in said plurality of subjects.

* * * * *